United States Patent
Vidal et al.

(10) Patent No.: US 9,375,206 B2
(45) Date of Patent: Jun. 28, 2016

(54) SURGICAL INSTRUMENT WITH DISENGAGEABLE HANDLE

(75) Inventors: Clement Vidal, Grenoble (FR); Herve Collet, Chatenay (FR); Patrick Henri, Bois Colombes (FR)

(73) Assignee: ENDOCONTROL, La Tronche (FR)

( * ) Notice: Subject to any disclaimer, the term of this patent is extended or adjusted under 35 U.S.C. 154(b) by 0 days.

(21) Appl. No.: 14/240,023

(22) PCT Filed: Aug. 24, 2012

(86) PCT No.: PCT/EP2012/066494
§ 371 (c)(1),
(2), (4) Date: Feb. 20, 2014

(87) PCT Pub. No.: WO2013/026920
PCT Pub. Date: Feb. 28, 2013

(65) Prior Publication Data
US 2014/0200594 A1    Jul. 17, 2014

Related U.S. Application Data

(60) Provisional application No. 61/527,519, filed on Aug. 25, 2011.

(30) Foreign Application Priority Data

Aug. 26, 2011  (EP) .................................... 11306065
Aug. 26, 2011  (EP) .................................... 11306066

(51) Int. Cl.
  *A61B 17/04*  (2006.01)
  *A61B 17/00*  (2006.01)
  *A61B 17/29*  (2006.01)

(52) U.S. Cl.
CPC ........... *A61B 17/00234* (2013.01); *A61B 17/00* (2013.01); *A61B 17/2909* (2013.01);
(Continued)

(58) Field of Classification Search
CPC ............. A61B 17/00; A61B 17/00234; A61B 17/2909; A61B 2017/00398; A61B 2017/2923; A61B 2017/0042; A61B 2017/2927; A61B 2017/00367; A61B 2017/00738; A61B 2017/2929; A61B 2017/003; A61B 2017/291
USPC .......................... 606/148, 167, 169, 170, 180
See application file for complete search history.

(56) References Cited

U.S. PATENT DOCUMENTS 5,297,443 A    3/1994   Wentz
5,553,675 A    9/1996   Pitzen et al.
(Continued)

FOREIGN PATENT DOCUMENTS

DE    20 2004 006 659 U1    8/2004
EP         0 834 891 A2    4/1998
(Continued)

OTHER PUBLICATIONS

Final Office Action in U.S. Appl. No. 14/240,022 dated Aug. 4, 2015. 13 pages.

*Primary Examiner* — Ashley Fishback
(74) *Attorney, Agent, or Firm* — Blakely Sokoloff Taylor & Zafman LLP

(57) ABSTRACT

The invention relates to a surgical instrument comprising: —a distal tool (5) securely fastened to a distal end of a rotation shaft (4) and rotatably mounted on and in the extension of a distal member (30) rotatably mounted at an end of an elongated arm (3), —an comprising motorized means (20) for actuating the distal motion of the distal tool (5) and further comprising controlling means (21) for a user to control the motorized means (20); —a handle (1) extending from the actuation unit (2) and comprising a lever (11) mechanically coupled to the distal tool (5) for actuation of said distal tool (5); characterized in that the handle (1) has a non-axially-symmetric shape and is mounted on and in the extension of the actuation unit (2) with coupling means (12, 22) enabling rotation of the handle (1) relative to the actuation unit (2) around the longitudinal axis, and wherein the controlling means (21) are adapted to be operated by the user whatever the rotational position of the handle (1) relative to the actuation unit (2).

16 Claims, 7 Drawing Sheets

(52) U.S. Cl.
CPC ... *A61B2017/003* (2013.01); *A61B 2017/0042* (2013.01); *A61B 2017/00367* (2013.01); *A61B 2017/00398* (2013.01); *A61B 2017/00738* (2013.01); *A61B 2017/291* (2013.01); *A61B 2017/2923* (2013.01); *A61B 2017/2927* (2013.01); *A61B 2017/2929* (2013.01)

(56) References Cited

U.S. PATENT DOCUMENTS

| | | |
|---|---|---|
| 5,984,939 A | 11/1999 | Yoon |
| 6,442,011 B1 | 8/2002 | Attarian et al. |
| 6,913,613 B2 | 7/2005 | Schwarz et al. |
| 7,147,650 B2 | 12/2006 | Lee |
| 7,241,288 B2 | 7/2007 | Braun |
| 7,316,681 B2 | 1/2008 | Madhani et al. |
| 7,338,513 B2 | 3/2008 | Lee et al. |
| 7,398,707 B2 | 7/2008 | Morley et al. |
| 7,686,826 B2 | 3/2010 | Lee et al. |
| 7,842,028 B2 | 11/2010 | Lee |
| 2002/0087179 A1* | 7/2002 | Culp et al. ............ 606/167 |
| 2004/0193146 A1 | 9/2004 | Lee et al. |
| 2006/0095074 A1 | 5/2006 | Lee et al. |
| 2006/0111210 A1 | 5/2006 | Hinman |
| 2007/0088340 A1 | 4/2007 | Brock et al. |
| 2007/0162404 A1 | 7/2007 | Gorelik et al. |
| 2007/0250113 A1 | 10/2007 | Hegeman et al. |
| 2008/0039255 A1 | 2/2008 | Jinno et al. |
| 2008/0091072 A1 | 4/2008 | Omori et al. |
| 2008/0228196 A1 | 9/2008 | Wang et al. |
| 2008/0300458 A1 | 12/2008 | Kim et al. |
| 2009/0030428 A1 | 1/2009 | Omori et al. |
| 2009/0107287 A1 | 4/2009 | Seki |
| 2010/0016852 A1 | 1/2010 | Manzo et al. |
| 2010/0168722 A1 | 7/2010 | Lee et al. |
| 2010/0228284 A1 | 9/2010 | Cooper et al. |
| 2010/0249497 A1 | 9/2010 | Peine et al. |
| 2010/0286480 A1 | 11/2010 | Peine et al. |
| 2010/0331860 A1 | 12/2010 | Barrier et al. |
| 2011/0017801 A1 | 1/2011 | Zemlok et al. |
| 2011/0198385 A1 | 8/2011 | Whitman et al. |
| 2011/0227568 A1 | 9/2011 | Dordet et al. |
| 2011/0234369 A1 | 9/2011 | Cai et al. |
| 2011/0298452 A1 | 12/2011 | Mao |

FOREIGN PATENT DOCUMENTS

| | | |
|---|---|---|
| EP | 0 834 891 A3 | 11/1998 |
| WO | WO 2010/009525 A1 | 1/2010 |
| WO | WO 2010/112608 A1 | 10/2010 |
| WO | WO 2010/112609 A1 | 10/2010 |
| WO | WO 2011/013100 A1 | 2/2011 |

* cited by examiner

Fig. 1
Fig. 2
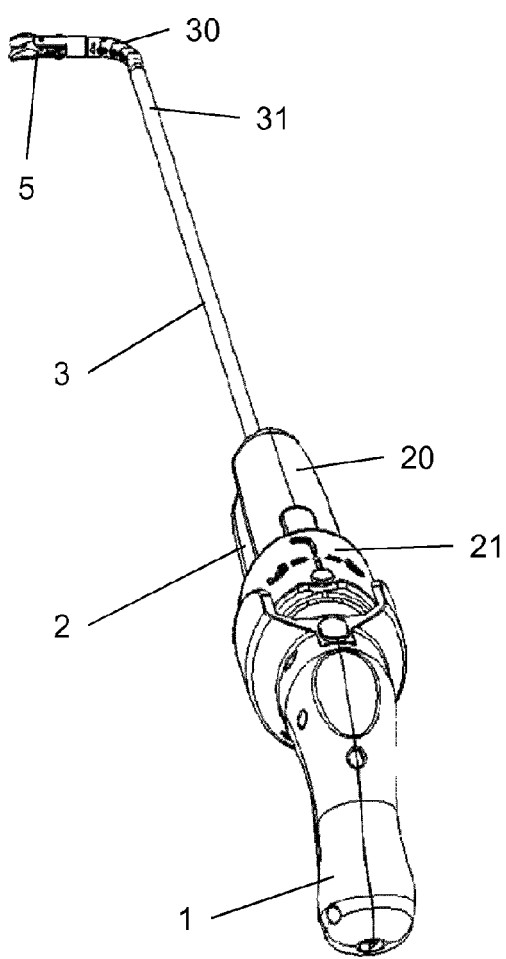
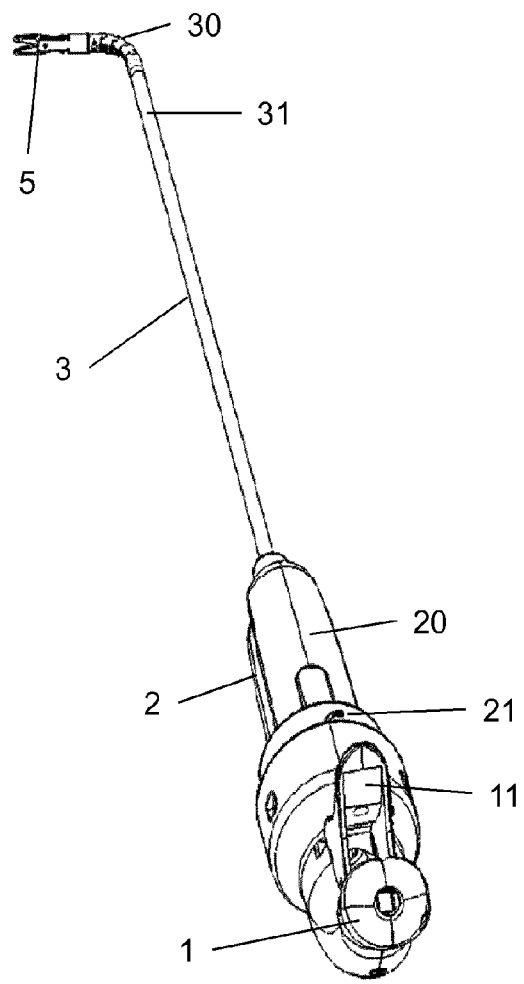

SURGICAL INSTRUMENT WITH DISENGAGEABLE HANDLE

FIELD OF THE INVENTION

The invention relates to a surgical instrument designed for endoscopic or laparoscopic surgical operations.

TECHNICAL BACKGROUND

Within the scope of minimally-invasive surgery, such as endoscopic or laparoscopic surgery, access to the operating site is made via small incisions in the body of the patient (such as the abdomen or thorax), in which the practitioner places a cannula formed by a tube whereof the diameter varies from 3 to 15 mm, via which the practitioner can insert into the body of the patient either an endoscope for obtaining a video image on a monitor, or long and fine instruments for performing a procedure at the operating site.

The majority of existing instruments is constituted by a fine (typically around 5 mm in diameter) and rigid elongated body (typically around 30 cm long). The proximal end of the instrument comprises a grip handle for the practitioner and the distal end of the instrument is often fitted with a forceps or scissors, optionally capable of transmitting electric current for cutting (monopolar or bipolar).

The main advantage of laparoscopic surgery is the minimum incisions. However, the main limitation is the decrease in dexterity associated with a remote access by long instruments. Indeed, when the instrument is rigid, its passage via a fixed incision point is a planar kinematic constraint which limits the number of degrees of freedom (DoF) to four, i.e. three movements of rotation about the point of incision and a penetration translation movement of the instrument. In particular, with conventional laparoscopic rigid instruments, it is impossible to bend the distal end of the instrument to orient the forceps optimally relative to the practitioner. This is a major application limitation of laparoscopic surgical tools for surgical procedures.

This has led to the development of novel instruments comprising a distal part exhibiting mobility relative to the principal body of the instrument. For example, for suturing exercise, the surgeon uses a curved needle. When he carries out this exercise in optimal conditions, the surgeon:
1. grasps the needle such that the plane of the needle is perpendicular to the axis of the forceps;
2. places the plane of the needle perpendicularly to the edges to be sutured;
3. turns the needle according to an axis perpendicular to its plane to insert it into the tissue to be sutured.

Therefore, to make a suture in favorable conditions, there must be means for placing the axis of the instrument substantially parallel to the edges to be sutured and turning the forceps about its axis. During some interventions, positioning the points of incision relative to the operating site is such that it is not possible to align the axis of the forceps with the edges to be sutured when using rigid instruments, substantially complicating the way to make the suture. Thus instruments have been developed which are adapted for orienting the axis of the forceps relative to the principal axis of insertion of the instrument in the body, due to distal mobility.

It should be noted that the final rotation movement of the forceps around its own axis (intrinsic rotation of the forceps), which controls penetration of the needle, must be made with a high precision and a maximal stability of the direction of the axis of the forceps while applying sufficient force to perforate tissue.

There have been a lot of different developments of surgical instruments having a distal mobility. Generally, these surgical instruments are such that the axis of the forceps can be oriented relative to the main axis of insertion of the instrument through a rotation made about any axis perpendicular to such main axis of insertion. These instruments may be supported by a robotic arm but are more often hand held.

With these kind instruments, the user further wants to be able to orient the axis of the forceps in any direction relative to the main axis of insertion of the instrument. This requires that the forceps is mounted with two orthogonal pivot joints on the instrument shaft and that each pivot joint has a 180° range of motion to provide a right angle orientation of the forceps in both directions. Instruments fulfilling this requirement have for instance been described in U.S. Pat. Nos. 7,147,650, 7,338,513, 7,686,826, 7,842,028, US2006111210, US2007250113, US2010286480, or US2010331860. However the more complex the joint between the forceps and the instrument shaft, the bigger the joint. Moreover overall instrument diameter is an issue in minimally invasive surgery where 5 mm diameter is a gold standard. Some have chosen to use flexible material in between shaft and forceps to reduce joint diameter, but it then compromises overall strength and rigidity. Further, most of the proposed solutions can unfortunately not be adapted for motorization of the motion of the forceps—or any other distal tool—which is a major drawback since motion of such distal tool generally need to be very accurate.

In WO2010112608 and WO2010112609, is described an instrument having a forceps mounted on an outer arm comprising a pivot joint around a single axis. This enables using assembly element such as vertebrae which provide a good resistance to forces applied off the plane that is perpendicular to the pivot axis. Also, when the instrument is motorized, using one pivot only exhibits the advantage of requiring only one actuator dedicated to the orientation of the forceps. However as described above, this does not allow to orient forceps in any direction.

A solution to overcome this problem is to use a further rotation around the insertion axis. This rotation can for instance be manually controlled by the surgeon at the handle level. However, a drawback to this hand rotation is the limited range of possible rotation, induced by the limited range of human wrist motion. When handling an instrument handle, it can be considered that the maximum range of rotation is 180° degrees, which is the range of the pronation-supination wrist motion. If a 360° rotation is required, it may be used the instrument described in WO2011013100 that comprises a handle and control means with a cylindrical symmetry, which enables the user to rotate the instrument in its hand and to still be able to use instrument normally (no preferential orientation). However, manipulating such an inline instrument imposes the user to put elbow up which involves shoulder abduction. This anatomical posture is known not to be ergonomic in the long run.

In US2010249497 it has been proposed two different embodiments of a surgical instrument provided with means to orbit the distal tool relative to the longitudinal axis of the main shaft, said orbit of the distal tool being made by an own rotation of the instrument shaft. The first embodiment which is disclosed in this document is fully manually operated, with only mechanical coupling. In particular, there is proposed to use a mechanical ball & neck assembly for manually actuating the bending of the distal tool. The second embodiment disclosed in US2010249497 comprises a motorized push/pull cable drive mechanism that replaces the ball & neck assembly. The motorized assembly does however complexify the structure of the surgical instrument. In particular, an own rotation of the distal tool can only be operated by combination of the pivot and orbit movements of the tool, more precisely a combination of the own rotation of the instrument shaft and two pivots of the distal tool made about two axis perpendicular to the longitudinal axis of the instrument and perpendicular to each other. However, such combination of movements necessarily requires an electronic control of the corresponding motors, which complexifies the instrument. Such surgical instrument has further the drawback of being relatively voluminous, when full motorization is used.

A goal of the present invention is thus to propose a surgical instrument that does not present the above drawbacks.

More precisely, a goal of the present invention is to propose a surgical instrument that enables the distal tool to have any desired position, where control of the motion of the distal tool being very accurate, and which manipulation is easy and comfortable for the surgeon.

Another goal of the present invention is to propose a surgical instrument with an innovative actuation mechanism of the bending motion of the distal tool.

SUMMARY OF THE INVENTION

To this end, is proposed a surgical instrument as defined in the appended claims.

According to a first aspect, it is proposed a surgical instrument comprising:
  an elongated arm extending along a longitudinal axis and having a distal member mounted at a distal end of the elongated arm with means forming a pivot joint around a pivot axis orthogonal to the longitudinal axis;
  a rotation shaft coaxial with the elongated arm comprising means forming a universal joint facing the pivot joint;
  a distal tool securely fastened at a distal end of the rotation shaft and rotatably mounted on and in the extension of the distal member of the elongated arm, such that the distal tool has two rotational degrees of freedom, distinct and independent of each other, one degree of freedom being around the pivot axis and the other degree of freedom being around an axis collinear to an own axis of the distal tool;
  an actuation unit mounted on and in the extension of a proximal end of the elongated arm, said actuation unit comprising motorized means for actuating the motion of the distal tool through at least one of the two rotational degrees of freedom and further comprising controlling means for a user to control the motorized means;
  a handle extending from the actuation unit and comprising a lever mechanically coupled to the distal tool for actuation of said distal tool via an actuation cable extending coaxially within said elongated arm and rotation shaft;
  characterized in that the handle has a non-axially-symmetric shape and is mounted on and in the extension of the actuation unit with coupling means enabling rotation of the handle relative to the actuation unit around the longitudinal axis, and wherein the controlling means are adapted to be operated by the user whatever the rotational position of the handle relative to the actuation unit.

Preferable but not limited aspects of such surgical instrument, taken alone or in combination, are the following:
  the actuation unit comprises a casing for receiving the motorized means and the controlling means.
  the casing comprises prehensile means for holding the surgical instrument while rotating the handle and the actuation unit relative to one another.
  the lever is coupled to the actuation cable with a transmission mechanism being non-axial for enabling an electric cable to run axially out of the actuation unit along the longitudinal axis from the motorized means to the handle.
  the transmission mechanism comprises:
    at least one rod arranged within the actuation unit offset of the longitudinal axis, said rod being translatable along an axis parallel to the longitudinal axis;
    a coupling member between said rod and the actuation cable, said coupling member being shaped and arranged to transmit the translation motion of the rod to the actuation cable and to enable a free rotation of the actuation cable around the longitudinal axis;
    an annular member arranged within the actuation unit to be coupled with the lever of the handle, said annular member being fixed to an end of said rod, and said annular member being arranged to surround the electric cable and to be translatable along an axis parallel to the longitudinal axis;
    and wherein the annular member further comprises a circular groove for insertion of at least two pins provided at an end of the lever, said circular groove and pins forming a coupling enabling the lever to cause the annular member and rod to translate while enabling a free rotation of the handle and lever relative to the actuation unit.
  the controlling means comprise electronic components for actuation of the motorized means, and switch elements for the user to control the electronic components, wherein the motorized means and electronic components are enclosed in a sealed compartment.
  the switch elements are located out of the sealed compartment, said switch elements and electronic components comprising means for contactless signal transmission.
  the switch elements comprise at least one magnet for contactless signal transmission to hall sensors of the electronic components.
  the at least one magnet is mounted on the sealed compartment and arranged to be displaced through two different degrees of freedom in order to vary the position of the magnet relative to the hall sensors.
  the switch elements comprise one magnet, an outer knob and an inner knob, wherein the magnet is fastened to the outer knob and is mounted in translation within a longitudinal groove provided in the inner knob along an axis parallel to the longitudinal axis, said inner knob being rotatably mounted around the longitudinal axis.
  the switch elements comprise at least eight hall sensors, two of said at least eight hall sensors being arranged for providing signal to the motorized means upon translation of the outer knob, two others of said at least eight hall sensors being arranged for providing signal to the motorized means upon rotation of the outer knob, and the four remaining of said at least eight hall sensors being arranged for providing signal to the motorized means upon combined translation and rotation of the outer knob.
  the hall sensors are used as potentiometers, preferably for controlling the speed of the motorized means.
  a translation of the outer knob controls the motorized means for actuation of the distal tool through a rotation around the pivot axis, and wherein a rotation of the outer knob controls the motorized means for actuation of the distal tool through a rotation around the axis collinear to the own axis of the distal tool.

the coupling means comprise a clutch assembly for preventing rotation of the handle relative to the actuation unit.

According to another aspect, there is provided a surgical instrument comprising:
- an elongated arm extending along a longitudinal axis and having a distal member mounted at a distal end of the elongated arm with means forming a pivot joint around a pivot axis orthogonal to the longitudinal axis;
- a rotation shaft coaxial with the elongated arm comprising means forming a universal joint facing the pivot joint;
- a distal tool securely fastened at a distal end of the rotation shaft and rotatably mounted on and in the extension of the distal member of the elongated arm, such that the distal tool has two rotational degrees of freedom, distinct and independent of each other, one degree of freedom being around the pivot axis and the other degree of freedom being around an axis collinear to an own axis of the distal tool;
- an actuation unit mounted on and in the extension of a proximal end of the elongated arm, said actuation unit comprising motorized means for actuating the motion of the distal tool through at least one of the two rotational degrees of freedom; and
- a first actuation cable and a second actuation cable arranged parallel to each other within the elongated arm along the longitudinal axis, said first and second actuation cables having each an end fastened to the distal member so that translation of one of the first and second actuation cables relative to the other one of the first and second actuation cables actuates the distal tool through the rotation around the pivot axis;

characterized in that the motorized means comprise a motor with a driving shaft having first and second transmission members for coupling the driving shaft with the first and second actuation cables respectively, wherein the first transmission member comprises means for translating the first actuation cable in a first direction collinear to the longitudinal axis upon clockwise rotation of the driving shaft, and the second transmission member comprises means for translating the second actuation cable in the first direction upon anticlockwise rotation of the driving shaft.

Preferable but not limited aspects of such surgical instrument, taken alone or in combination, are the following:
- the first and second transmission members are coupled to the driving shaft with coupling means adapted for translating the transmission members in opposite directions along the longitudinal axis of the driving shaft upon rotation of the driving shaft of the motor.
- the driving shaft comprises a first threaded portion and a second threaded portion for cooperation with a first threaded bore of the first transmission member and with a second threaded bore of the second transmission member respectively, wherein said first and second threaded portions have opposite threads.
- the first and second threaded portions have different pitches.
- the first transmission member comprises means for releasing the first actuation cable upon anticlockwise rotation of the driving shaft, and the second transmission member comprises means for releasing the second actuation cable upon clockwise rotation of the driving shaft.
- the first, respectively second, actuation cable comprises an abutment adapted to cooperate with the first, respectively second, transmission member so that translation of the first, respectively second, transmission member in the first direction causes the first, respectively second, actuation cable to translate in said first direction, whereas a translation of the first, respectively second, transmission member in a second direction opposite the first direction releases the first, respectively second, actuation cable.
- the first, respectively second, actuation cable comprises an end with a threaded portion and a threaded bolt mounted on said threaded portion for adjustment of the length of said first, respectively second, actuation cable, said threaded bolt forming the abutment.
- the first transmission member comprises means for translating the first actuation cable in a second direction opposite to the first direction upon anticlockwise rotation of the driving shaft, and the second transmission member comprises means for translating the second actuation cable in the second direction upon clockwise rotation of the driving shaft.
- the first, respectively second, actuation cable has an end securely fastened to the first, respectively second, transmission member.
- the motorized means comprise another motor with another driving shaft fixed to an end of the rotation shaft for actuating rotation of the distal tool around the axis collinear to the own axis of said distal tool.
- the surgical instrument further comprises electronic components for actuation of the motorized means and switch elements for a user to control the electronic components, wherein the motorized means and electronic components are enclosed in a sealed compartment, the switch elements being located out of said sealed compartment, and wherein the switch elements and electronic components comprise means for contactless signal transmission.
- the switch elements comprise at least one magnet for contactless signal transmission to hall sensors of the electronic components.
- the at least one magnet is mounted on the sealed compartment and arranged to be displaced through two different degrees of freedom in order to vary the position of the magnet relative to the hall sensors.
- the switch elements comprise one magnet, an outer knob and an inner knob, wherein the magnet is fastened to the outer knob and is mounted in translation within a longitudinal groove provided in the inner knob along an axis parallel to the longitudinal axis, said inner knob being rotatably mounted around the longitudinal axis.
- the hall sensors are used as potentiometers, preferably for controlling the speed of the motorized means.

According to still another aspect, there is provided a surgical instrument comprising:
- an elongated arm extending along a longitudinal axis and having a distal member mounted at a distal end of the elongated arm with means forming a pivot joint around a pivot axis orthogonal to the longitudinal axis;
- a rotation shaft coaxial with the elongated arm comprising means forming a universal joint facing the pivot joint;
- a distal tool securely fastened at a distal end of the rotation shaft and rotatably mounted on and in the extension of the distal member of the elongated arm, such that the distal tool has two rotational degrees of freedom, distinct and independent of each other, one degree of freedom being around the pivot axis and the other degree of freedom being around an axis collinear to an own axis of the distal tool;
- an actuation unit mounted on and in the extension of a proximal end of the elongated arm, said actuation unit comprising motorized means for actuating the motion of the distal tool through the two rotational degrees of freedom, and further comprising controlling means for a user to control the motorized means; and a handle extending from the actuation unit;

characterized in that the controlling means comprise electronic components for actuation of the motorized means, and switch elements for the user to control the electronic components, the switch elements comprising at least one magnet for contactless signal transmission to hall sensors of the electronic components, wherein the switch elements comprise an outer knob and an inner knob, with the magnet being fastened to the outer knob and being mounted in translation within a longitudinal groove provided in the inner knob along an axis parallel to the longitudinal axis, said inner knob being rotatably mounted around the longitudinal axis.

Preferable but not limited aspects of such surgical instrument, taken alone or in combination, are the following:

- the motorized means and electronic components are enclosed in a sealed compartment, the switch elements being located out of said sealed compartment.
- the switch elements comprise at least eight hall sensors, two of said at least eight hall sensors being arranged for providing signal to the motorized means upon translation of the outer knob, two others of said at least eight hall sensors being arranged for providing signal to the motorized means upon rotation of the outer knob, and the four remaining of said at least eight hall sensors being arranged for providing signal to the motorized means upon combined translation and rotation of the outer knob.
- the hall sensors are used as potentiometers.
- the hall sensors are used for controlling the speed of the motorized means.
- a translation of the outer knob controls the motorized means for actuation of the distal tool through a rotation around the pivot axis, and wherein a rotation of the outer knob controls the motorized means for actuation of the distal tool through a rotation around the axis collinear to the own axis of the distal tool.
- the handle comprises a lever mechanically coupled to the distal tool for actuation of said distal tool via an actuation cable extending coaxially within said elongated arm and rotation shaft.
- the actuation unit further comprises complementary motorized means for actuation of said distal tool via an actuation cable extending coaxially within said elongated arm and rotation shaft.
- the surgical instrument further comprises a first actuation cable and a second actuation cable arranged parallel to each other within the elongated arm along the longitudinal axis, said first and second actuation cables having each an end fastened to the distal member so that translation of one of the first and second actuation cables relative to the other one of the first and second actuation cables actuates the distal tool through the rotation around the pivot axis, wherein the motorized means comprise a motor with a driving shaft having first and second transmission members for coupling the driving shaft with the first and second actuation cables respectively, wherein the first transmission member comprises means for translating the first actuation cable in a first direction collinear to the longitudinal axis upon clockwise rotation of the driving shaft, and the second transmission member comprises means for translating the second actuation cable in the first direction upon anticlockwise rotation of the driving shaft.
- the first and second transmission members are coupled to the driving shaft with coupling means adapted for translating the transmission members in opposite directions along the longitudinal axis of the driving shaft upon rotation of the driving shaft of the motor.
- the driving shaft comprises a first threaded portion and a second threaded portion for cooperation with a first threaded bore of the first transmission member and with a second threaded bore of the second transmission member respectively, wherein said first and second threaded portions have opposite threads.
- the first and second threaded portions have different pitches.
- the first transmission member comprises means for releasing the first actuation cable upon anticlockwise rotation of the driving shaft, and the second transmission member comprises means for releasing the second actuation cable upon clockwise rotation of the driving shaft.
- the first, respectively second, actuation cable comprises an abutment adapted to cooperate with the first, respectively second, transmission member so that translation of the first, respectively second, transmission member in the first direction causes the first, respectively second, actuation cable to translate in said first direction, whereas a translation of the first, respectively second, transmission member in a second direction opposite the first direction releases the first, respectively second, actuation cable.
- the first, respectively second, actuation cable comprises an end with a threaded portion and a threaded bolt mounted on said threaded portion for adjustment of the length of said first, respectively second, actuation cable, said threaded bolt forming the abutment.
- the first transmission member comprises means for translating the first actuation cable in a second direction opposite to the first direction upon anticlockwise rotation of the driving shaft, and the second transmission member comprises means for translating the second actuation cable in the second direction upon clockwise rotation of the driving shaft.
- the first, respectively second, actuation cable has an end securely fastened to the first, respectively second, transmission member.
- the motorized means comprise another motor with another driving shaft fixed to an end of the rotation shaft for actuating rotation of the distal tool around the axis collinear to the own axis of said distal tool.

BRIEF DESCRIPTION OF THE DRAWINGS

Other characteristics and advantages of the invention will become clear from the following description which is only given for illustrative purposes and is in no way imitative and should be read with reference to the attached drawings on which:

FIG. 1 is a perspective view of the surgical instrument of the invention, with the handle in a first position;

FIG. 2 is a perspective view of the surgical instrument of FIG. 1, with the handle in a second position opposite to the first position;

DETAILED DESCRIPTION OF THE DRAWINGS

Figure 3:
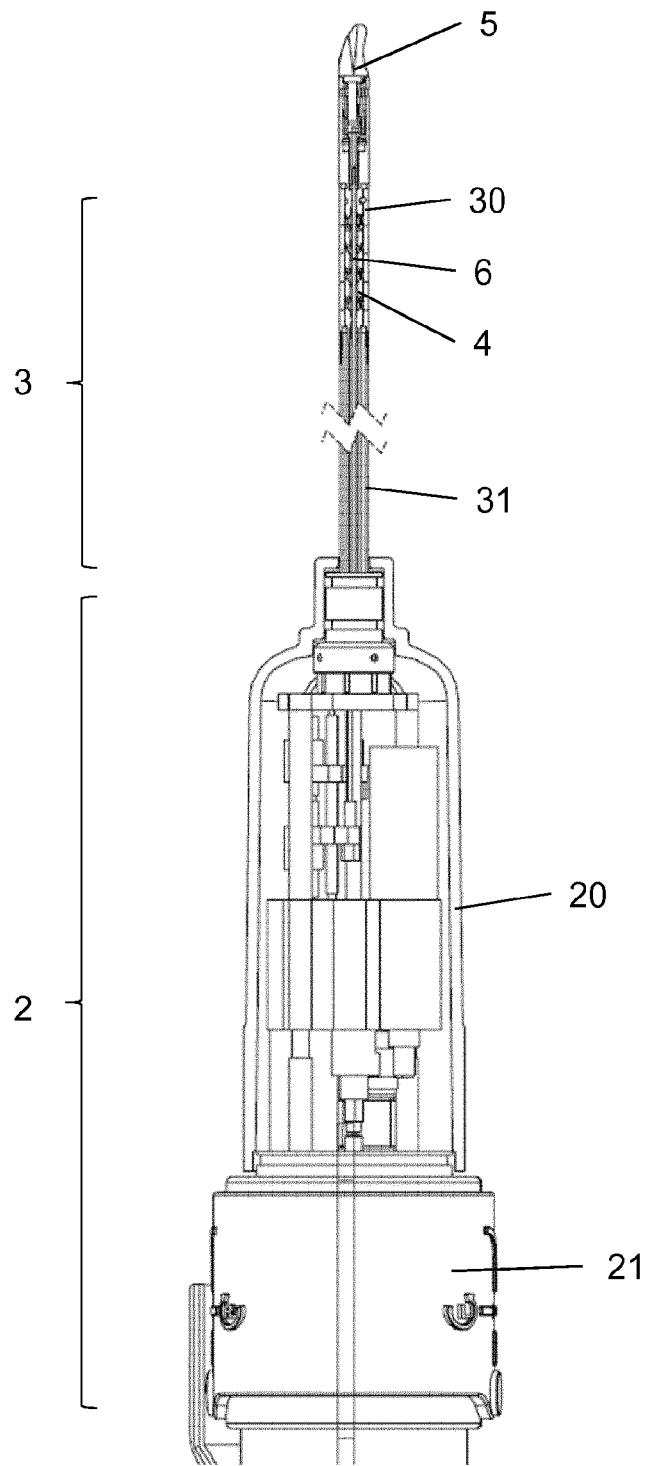
FIG. 3 is a partial cross sectioned view of the surgical instrument of the invention.
Figure 4:
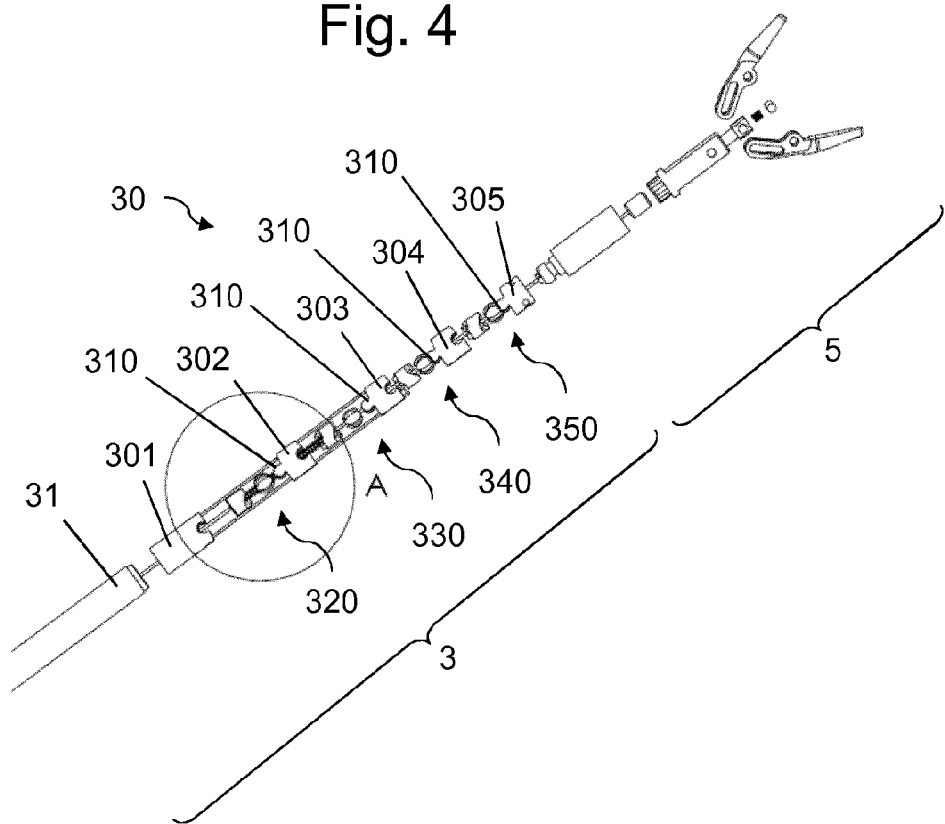
FIG. 4 is an exploded perspective view of a possible operational portion of a surgical instrument according the invention.
Figure 5:
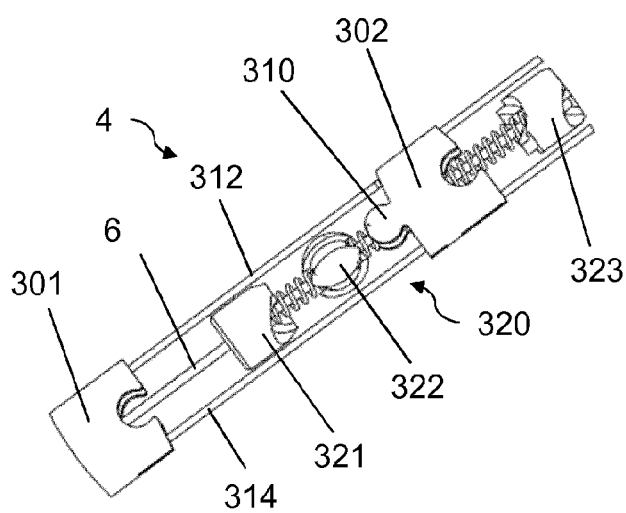
FIG. 5 is an enlarged view, in an exploded perspective view, of the portion referenced as A of the operational portion of FIG. 4.

The general structure of the surgical instrument of the invention is described in reference to FIGS. 1 to 3. Thus, the surgical instrument comprises:
- an elongated arm 3 extending along a longitudinal axis and having a distal member 30 mounted at a distal end 31 of the elongated arm 3 with means forming a pivot joint around a pivot axis orthogonal to the longitudinal axis;
- a rotation shaft 4 coaxial with the elongated arm 3 comprising means forming a universal joint facing the pivot joint;
- a distal tool 5—for instance a forceps—securely fastened at a distal end of the rotation shaft 4 and rotatably mounted on and in the extension of the distal member 30 of the elongated arm 3, such that the distal tool 5 has two rotational degrees of freedom, distinct and independent of each other, one degree of freedom being around the pivot axis and the other degree of freedom being around an axis collinear to an own axis of the distal tool;
- an actuation unit 2 mounted on and in the extension of a proximal end of the elongated arm 3, said actuation unit 2 comprising motorized means 20 for actuating the distal mobility of the tool, i.e. the motion of the distal tool through at least one of said two rotational degrees of freedom, and further comprising controlling means 21 for a user to control the motorized means 20;
- a handle 1 extending from the actuation unit 2.

Preferably, the handle 1 comprises a lever 11 mechanically coupled to the distal tool 5 for actuation of said distal tool 5 via an actuation cable extending coaxially within said elongated arm 3 and rotation shaft 4.

However, according to another embodiment, the handle 1 does not comprise any lever. In such case, the actuation unit 2 may comprise complementary motorized means for actuation of said distal tool 5 via an actuation cable 6 extending coaxially within said elongated arm 3 and rotation shaft 4.

It should here be noted that in conventional terms, a universal joint is a kinematic joint used for connecting two shafts and adapted for transmission of the rotational movement of one shaft to another, whatever the angular position of one shaft relative to the other is. There exist several types of universal joint.

Such arrangement for a surgical instrument enables direct transmission that produces an infinite rotation of the forceps about its own axis, without having to modify the position of the axis of the forceps, or reconfiguring movements or using a clutch system. All rotations are maintained and/or actuated independently. Further, all rotations may be actuated simultaneously if required. It is not necessary to reverse or cancel rotation to describe any movement on the other rotation. Because of this, distal movements are selected optimally to ensure simple control of the instrument while a suturing exercise for example is carried out.

The universal joint of the rotation shaft may for instance comprise a flexible drive sleeve, which is preferably rigid with regard to torsion stress according to the longitudinal axis, and is flexible and elastically deformable with regard to torsion stress according to any axis perpendicular to the longitudinal axis. For a detailed description of such arrangement, the person skilled in the art may refer to PCT application published as WO2010112608, the content of which is incorporated by reference.

Alternatively, the universal joint may comprise a Cardan joint. For a detailed description of such arrangement, the person skilled in the art may refer to PCT application published as WO2010112609, the content of which is incorporated by reference.

Basically, a Cardan joint consists of a mechanical linking system comprising two end elements mounted on either side of a central element, wherein each end element is mounted in a pivot joint with the central element, the axis of two pivot joints in the central element being perpendicular. Using a Cardan joint as universal joint in combination with linking elements mounted in series for forming the distal member of the elongated arm greatly simplifies manufacturing of the surgical instrument.

FIGS. 4 to 9 illustrate a specific embodiment of a surgical instrument wherein are used Cardan joints as universal joint in combination with linking elements mounted in series for forming the distal member. Here the elongated arm 3 comprises a plurality of linking elements making up the pivot function, where the set of linking elements can be similar to a set of hollow vertebrae, each of the vertebrae being mounted with a pivot joint about an axis perpendicular to the pivot axis of the elongated arm with the preceding vertebra. More precisely, the elongated arm 3 comprises a distal member 30 with five linking elements (301, 302, 303, 304, 305) forming the pivot joint (also called overall pivot joint). The elongated arm 3 is hollow and distally comprises a hollow base linking element 301, comprising one set of pivot lugs (female side only) extending in the direction of the distal end 31 of the elongated arm 3 and opposite one another to define an axis 310 substantially perpendicular to the longitudinal axis of the elongated arm 3. The elongated arm 3 further comprises hollow intermediate linking elements (302, 303, 304), comprising two lugs extending in the extension of said intermediate linking elements (302, 303, 304) and opposite one another to enable rotation about an axis parallel to the axis 310 of the base linking element 301 and located at a distal end of the intermediate linking elements (302, 303, 304). The intermediate linking element 302 is mounted in rotation relative to the axis 310 on the base linking element 301, thus forming a first limited pivot joint (also called wedged pivot joint, as the form of the linking elements naturally restrict the amplitude of the pivot). Similarly, the intermediate linking elements (302, 303, 304) are mounted in mutual rotation relative to an axis parallel to the axis 310, thus forming a second and third limited pivot joint. The elongated arm 3 further comprises a hollow end linking element 305. Similarly, the end linking element 305 is mounted in rotation relative to an axis parallel to the axis 310 on the final intermediate linking element 304, thus forming a fourth limited pivot joint. This end linking element 305 forms the distal end of the elongated arm 3. The series of the limited pivot joints produces an accumulative pivot with respect to the whole body, which corresponds to the overall pivot joint. All the axes of the pivot joints 310 are parallel such that the total angle of flexion is the sum of the angles of rotation between each pair of linking elements. In addition, the vertebrae are pierced to allow two cables (312, 314) placed on either side of the axis of the pivot 310 to slide. The cables (312, 314) are attached to the final vertebra and slide in the openings of the others, which allow all the pivots to be actuated after mounting and therefore flexes by pulling on one or the other of the two cables (312, 314).

Mounted substantially coaxially with the elongated arm 3, the surgical instrument comprises a rotation shaft 4 which extends in the elongated arm 3 from a proximal end of said elongated arm 3 to a proximal part of the base linking element 301. The rotation shaft 4 comprises, at its distal end, means forming a universal joint which extend in the cavity formed by the different linking elements, these means forming a universal joint comprising at least one Cardan joint. The means forming a universal joint preferably comprise at least two Cardan joints. To maintain the full range of motion (longitudinal and radial rotation), the means forming a universal joint more preferably comprise as many Cardan joints as pivot axes 310 formed by the vertebrae (301, 302, 303, 304, 305). Accordingly, in the example presented in FIGS. 4 to 9, four Cardan joints (320, 330, 340, 350) are provided, respectively positioned at the level of the pivot axes 310 formed between the different linking elements (301, 302, 303, 304, 305), that is adjacent to the corresponding pivot joint. According to a preferred aspect of this embodiment, the axes of the two pivot joints defining each Cardan joint intersect with the pivot axis 310 at the level where it is positioned. As pointed out earlier, a Cardan joint is a mechanical linking system comprising two end elements mounted on either side of a central element, where each end element is mounted in a pivot joint with the central element. In the embodiment presented in FIGS. 4 to 9, the pivot joints between the pieces forming the Cardan joint are made by a sliding guide of one surface on another. To achieve this, end pieces having at their end of the surfaces sliding on the surface of the central piece can be provided for example, these central and end pieces also comprising sliding guide means.

A distal tool 5, for example a forceps, is mounted on a distal end of the end linking element 305, in its extension. The distal tool 5 is mounted in rotation about a longitudinal axis of the end linking element 305 on the latter. This distal tool 5 is preferably actuated by an actuation cable 6 extending inside the elongated arm 3, for instance an actuation cable 6 arranged to close the forceps 5 when pulled through activation of the lever 11. More preferably, the pieces forming the transmission by Cardan joints are pierced by through-holes along the main axis of the instrument when the latter is not flexed. These various holes made in the pieces of the Cardan joints allow a mechanical actuation cable 6 to pass through for transmission of traction force to actuate the distal tool 5 placed at the distal end of the instrument, or of electric cables (not shown) for transmission of a signal, a command or a monopolar and/or bipolar current.

Figure 6:
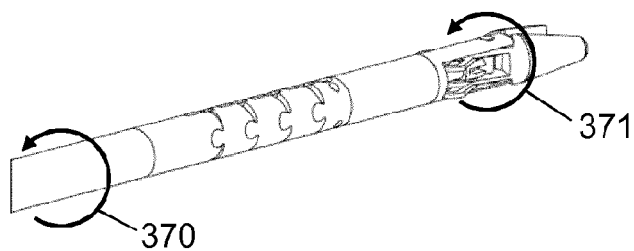
FIG. 6 is a perspective view of the operational portion of FIG. 4, the distal end being in a straight position.
Figure 7:
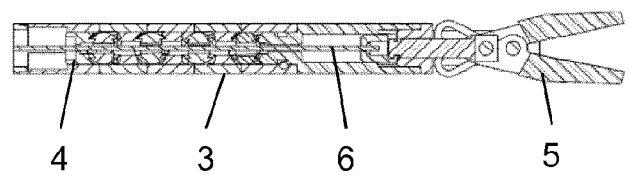
FIG. 7 is a cross sectioned view of the operational portion of FIG. 4, the distal end being in a straight position.
Figure 8:
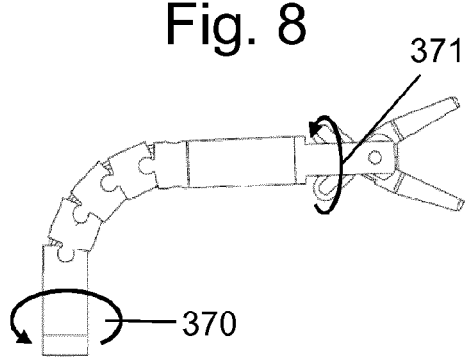
FIG. 8 is a perspective view of the operational portion of FIG. 4, the distal end being in a fully folded position.
Figure 9:
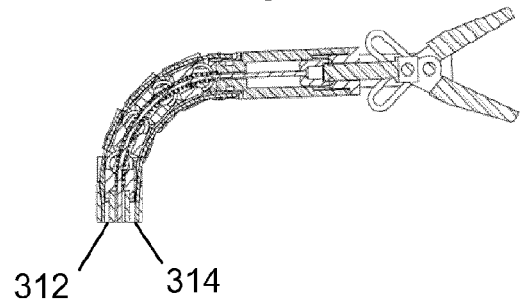
FIG. 9 is a cross sectioned view of the operational portion of FIG. 4, the distal end being in a fully folded position.

Operation of the surgical instrument is described with reference to FIGS. 8 and 9 that illustrate the folded position at 90°, and FIGS. 6 and 7 that illustrate the unfolded position. In both cases, a rotation movement 370 applied to the proximal end of the rotation shaft 4 causes rotation movement 371 of the distal tool 5. Perfect transmission of this rotation movement is ensured by the means forming a universal joint (eg. cardan joints 320, 330, 340, 350) and, this being irrespective of the angular deflection of the distal end turning about axes 310 of the limited pivot joints. The transition of the folded position to the unfolded position (or between the two different folded positions) occurs via translation movement of one of the cables 312, 314 according to its axis. An operator controls the bending of the distal tool 5 by translating one of these cables relative to the other.

Surgical instruments having a rotational symmetry around the longitudinal axis of said instrument do usually not enable ergonomic anatomical position, and force user to keep elbow up and shoulder abducted, which may lead to pain for the user in the long run. It is thus important for the surgical instrument to be provided with a non-axially-symmetric shape (i.e. having no rotational symmetry around the longitudinal axis of said instrument), such shape providing more ergonomic gripping members for the user. For instance, a pistol-grip handle allows the user to keep elbow down to avoid shoulder abduction or any other non-ergonomic anatomical position. It also allows the user to have improved gripping abilities, and thus get more accuracy in his gesture.

A specificity of the surgical instrument of the invention is that the handle 1 has an asymmetric shape, preferably a pistol-grip shape, and is mounted in the extension of the actuation unit 2 with coupling means forming a pivot joint about the longitudinal axis of the instrument. These coupling means thus enable rotation of the handle 1 relative to the actuation unit 2 around the longitudinal axis of the instrument.

The fact that the handle 1 is mounted in the extension of the actuation unit 2 means that the handle 1 and the actuation unit 2 are two distinct members, adjacent to one another, that are coupled together through a particular pivot joint.

Preferably, the actuation unit 2 comprises a casing that encompasses both the motorized means 20 and the controlling means 21. The handle 1 is thus rotatably mounted on this casing of the actuation unit 2, thereby forming a disengageable handle 1 relative to the actuation unit 2.

Further the controlling means 21 are adapted to be operated by the user from the handle 1, whatever the rotational position of the handle 1 relative to the actuation unit 2. Preferably, the controlling means 21 of the actuation unit 2 have a rotational symmetry around the longitudinal axis of the instrument so that the distal mobility can be actuated with the same hand position on the handle 1, whatever the rotational position of said handle relative to actuation unit 2.

The lever 11 arranged on the handle 1 to trigger the distal tool 5 through the actuation cable 6 is also oriented with the handle 1 so that the user can also actuate the tool without changing its hand position of the handle 1.

The distal rotation of the distal tool about the pivot axis—i.e. the bending of the instrument—is preferably restricted between 0° and 90°, such that one of the two extreme positions corresponds to the unbent configuration where the distal tool 5 is in line with the elongated arm 3. Thus, when the surgeon wants for instance to withdraw the surgical instrument from the cannula, he then only has to control the tool 5 to be at such extreme position to be sure that said tool 5 is in line with the elongated arm 3 which would not be the case if the bending ranged between −90° and 90°.

The proposed specific arrangement with the rotatable handle enables the surgical instrument to be used in any rotational position, in particular of the distal tool, which is of great advantages as it allows the surgeon to work at ease for any kind of surgical operation.

FIGS. 1 and 2 illustrate two opposed rotational positions of the handle 1 relative to the actuation unit 2. The orientation illustrated in FIG. 1 corresponds to the situation when the surgeon needs to work with the distal tool 5 oriented on the left-hand side of the surgical instrument. In case the surgeon has to work with the distal tool 5 oriented on the right-hand side of the surgical instrument, he then only has to rotate the handle 1 relative to the actuation unit 2 as illustrated in FIG. 2. As the controlling means 21 are adapted to be operated by the user in any rotational position of the handle 1, then the distal tool 5 may be easily oriented as required by the user. Preferably, the surgical instrument is adapted to position the handle 1 in any rotational position relative to the actuation unit 2, for instance when it is required to position the tool diagonally.

Preferably, the actuation unit 2 comprises an outer casing that is provided with prehensile means, that are adapted for grasping and holding the surgical instrument, either by hand or with any mechanical holding means (such as a robot). Consequently, when in use, it is possible for the user to hold in position the actuation unit 2, with no movement of the tool unit (including in particular the elongated arm 3, the rotation shaft 4, and the distal tool 5), while disengaging and rotating the handle 1 relative to the actuation unit 2. For instance, this allows the surgeon to angle the handle 1 to a more comfortable position, with more ease to proceed.

Figure 10:
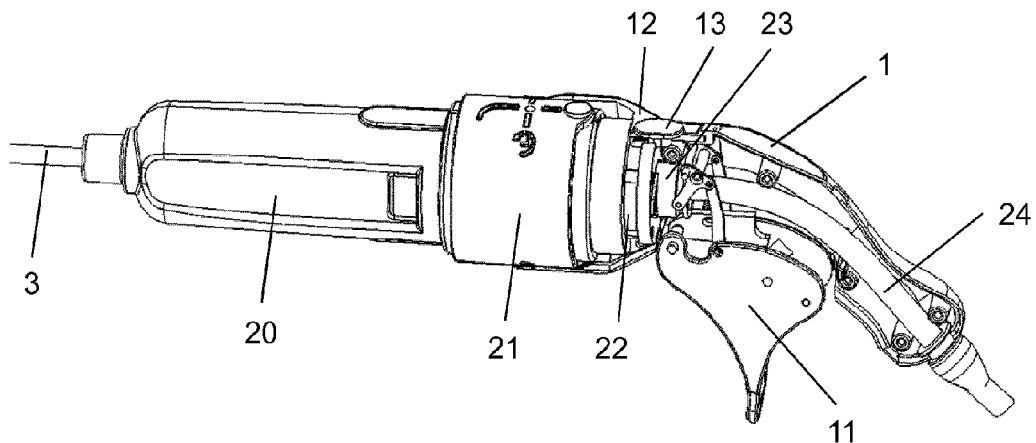
FIG. 10 is a perspective view of the handle and actuation unit of the surgical instrument of the invention.
Figure 11:
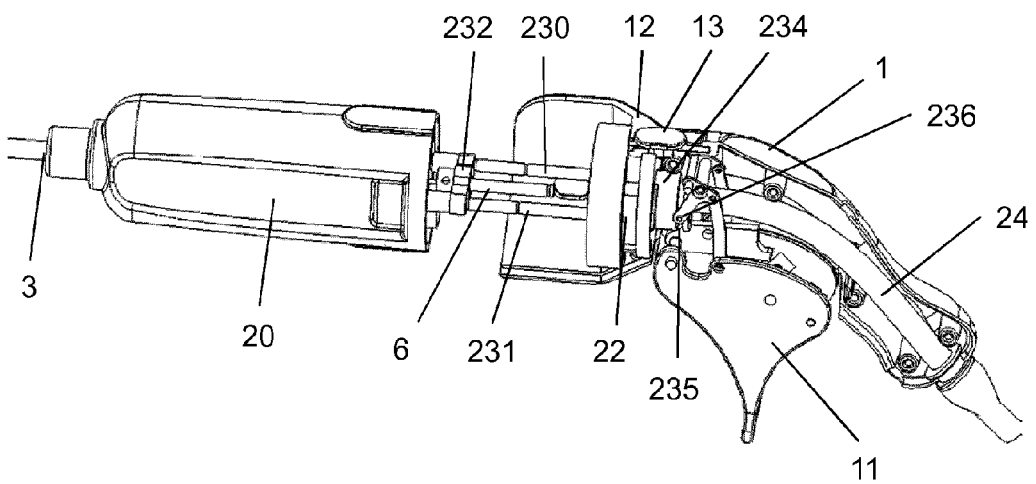
FIG. 11 is a similar perspective view as FIG. 10, illustrating the non-axial transmission mechanism.

Such arrangement is particularly advantageous as the handle 1 may be disengaged very easily and quickly, while preventing both the actuation unit 2 and the tool unit, and thus the distal tool 5, to be moved. FIGS. 10 and 11 illustrate a specific embodiment of the surgical instrument wherein the coupling means comprise two annular portions (12, 22) respectively provided in the actuation unit 2 and in the handle 1, said annular portions cooperating together for a relative rotation, e.g. through a circular groove and corresponding ridge. With such coupling means, the handle 1 may rotate on the annular portion 22 of the actuation unit 2. In the embodiment illustrated on FIG. 10, the actuation unit 2 has a substantially cylindrical shape.

Preferably, the coupling means comprise a clutch assembly 13 for locking the handle in position, by preventing rotation of the handle 1 relative to the actuation unit 2 when required. This enables maintaining the handle 1 in position relative to the actuation unit 2 when the surgeon uses the surgical instrument, such that the surgeon may move the instrument through an axial rotation about the longitudinal axis in addition to the distal mobility of the tool 5.

The distal mobility of the distal tool 5 is actuated by motorized means 20, which not only eases the work of the surgeon but also make his gesture much more accurate. Having motorized means 20, such as motors, however makes the configuration of the instrument more complex, in particular with regard to the arrangement of the rotatable handle 1 and the configuration of the controlling means 21.

The first issue relates to the motors and their arrangement in the instrument. It has been chosen to place the motorized means within the actuation unit 2 to keep most of the mechanical elements for actuating the distal mobility in a non-rotatable portion of the instrument, and thus to reduce the mechanical complications, in particular to avoid complex transmission of movement through the handle pivot articulation. The motorized means have however to be electrically connected to an external power source, and/or an external control unit for transfer of logic and power, such that an electric cable 24 is necessary. To avoid the surgeon to be bothered by such electric cable extending from the surgical instrument, it preferably runs from the motorized means 20 through the handle 1 out of the actuation unit 2.

As this electric cable 24 is connected into the actuation unit 2, it must be able to rotate with respect to user handle 1 while passing through said handle 1. To this end, the electric cable 24 shall be connected axially within the actuation unit 2, i.e. it should run along the longitudinal axis so that it keeps the same position whatever the rotational position of the handle 1 relative to the actuation unit 2. This avoids any rotation of the electric cable 24, and thus of the electric connections, which is important for ensuring long lifetime of the surgical instrument.

However, the mechanical cable 6 for actuating the operation of the distal tool 5, for instance for opening/closing a forceps, is traditionally axial as well. As electrical and mechanical cable cannot be made coaxial, a non-axial mechanism is used to transmit mechanical actuation of the distal tool 5 from the lever 11 of the handle 1. This non-axial transmission mechanism 23 enables offsetting the actuation elements from the lever 11 in the area where the electric cable 6 is located.

Figure 12:
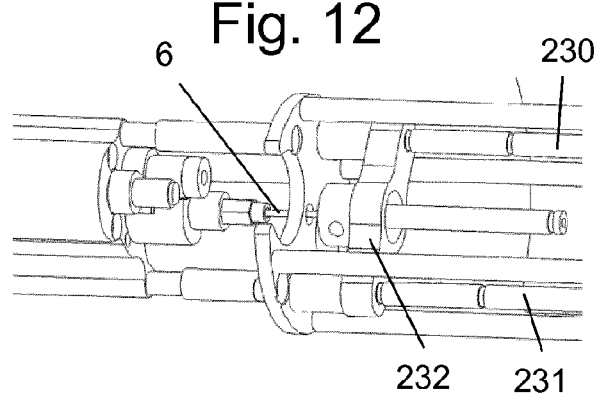
FIG. 12 is an enlarged perspective view of part of the actuation unit of the surgical instrument of the invention.

According to a particular embodiment illustrated in FIGS. 10 to 12, such transmission mechanism 23 comprises two rods 230 arranged within the actuation unit 2 offset of the longitudinal axis, said rods (230, 231) being translatable along an axis parallel to the longitudinal axis.

These two rods (230, 231) are both connected to a coupling member 232 that is connected to the actuation cable 6 directly coupled to the distal tool 5. Such coupling member 232 is preferably shaped and arranged to transmit the translation motion of the rods (230, 231) to the actuation cable 6 and to enable a free rotation of the actuation cable 6 around the longitudinal axis. This avoids torsion of the actuation cable 6 during axial rotation of distal tool 5 along the axis collinear to its own axis.

The non-axial transmission mechanism 23 further comprises an annular member 234 arranged within the actuation unit 2 to be coupled with the lever 11 of the handle 1. Such annular member 234 is fixed to an end of each of said two rods (230, 231) and is shaped and arranged to surround the electric cable 24 and to be translatable along an axis parallel to the longitudinal axis. This annular member 234 further comprises a circular groove 235 for insertion of at least two pins 236 provided at the end of the lever 11, so that the circular groove 235 and pins 236 form a coupling enabling the lever 11 to impart a translation motion to the annular member 234 and rods (230, 231) while enabling a free rotation of the handle 1 and lever 11 relative to the actuation unit 2. Indeed, when the handle 1 and lever 11 are rotated, the two pins 236 slide in the circular groove 235, and those pins 236 drive axial translation of the two rods (and thus actuation of the distal tool) whatever the rotation of the handle 1. This arrangement enables the lever 11 to translate the actuation cable 6 in any rotational position of the handle 1.

In FIG. 12, is illustrated the coupling between the two longitudinal rods (230, 231) running on each side of electrical cable 24 and the actuation cable 6 actuating operation of the distal tool. As described above, the actuation cable 6 can rotate freely along its longitudinal axis with respect to the two rods (230, 231) thanks to the coupling member 232. The actuation cable 6 then runs in the inner lumen of the axial rotation shaft 4, coaxially with the elongated arm 3, and finally within the distal member to be then fixed to the distal tool.

It should be noted that the above non-axial transmission mechanism does not necessary comprise only two rods, and that it may be adapted to comprise only a single rod arranged within the actuation unit 2 offset of the longitudinal axis, or more than two rods.

A second issue concerns the controlling means 21 of the motorized means 20 which have to be reachable by the user in any rotational position of the handle 1. A solution to that issue is to arrange the controlling means 21 so that they have a substantial axial symmetry along the longitudinal axis of the instrument, which thus enable the user to reach those controlling means 21 in any rotational position of the handle 1.

As illustrated in FIG. 10, the actuation unit 2 has preferably a cylindrical shape, and the controlling means have in this case an annular arrangement. It may for instance comprise an annular joystick 21 as illustrated in FIG. 11 that enables the user a finger control of the distal mobility, for example a thumb or forefinger control because of the pistol-grip shape of the handle 1.

The annular arrangement of the controlling means 21 could be implemented in various ways. However, to allow for steam sterilization of the instrument (gold standard for sterilization), motors and electronics are preferably placed in a sealed compartment, which thus influences the way the controlling means are structured.

To ensure perfect sealing of the instrument, it is recommended to limit mechanical movements through the sealed barrier. Thus, it is preferred to provide controlling means 21 adapted for contactless electronic communication, for instance between the electronics 210 located within the sealed compartment and a switch 211 located outside.

According to a preferred embodiment, the switch comprises a magnet 2110 outside the sealed compartment and a plurality of Hall sensors 2100 inside the sealed compartment. The magnet 2110 is arranged to be displaced laterally in two directions by the user. When such magnet 2110 is placed in front of Hall sensors 2100, the magnetic field modifications are detected by these Hall sensors 2100, creating an input signal, which is processed by the electronics to actuate the motors of the motorized means 20 for distal movement of the distal tool 5.

Figure 13:
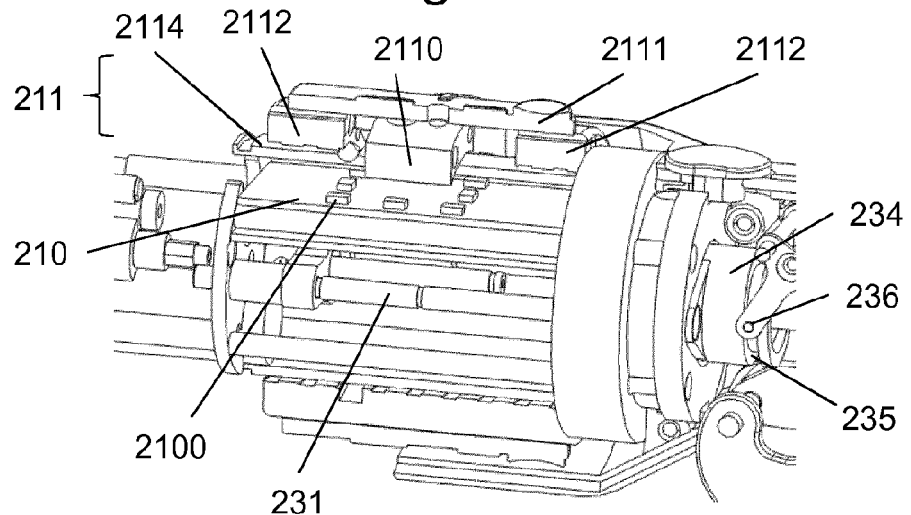
FIG. 13 is an enlarged perspective view of the controlling means of the actuation unit of the surgical instrument of the invention.
Figure 14:
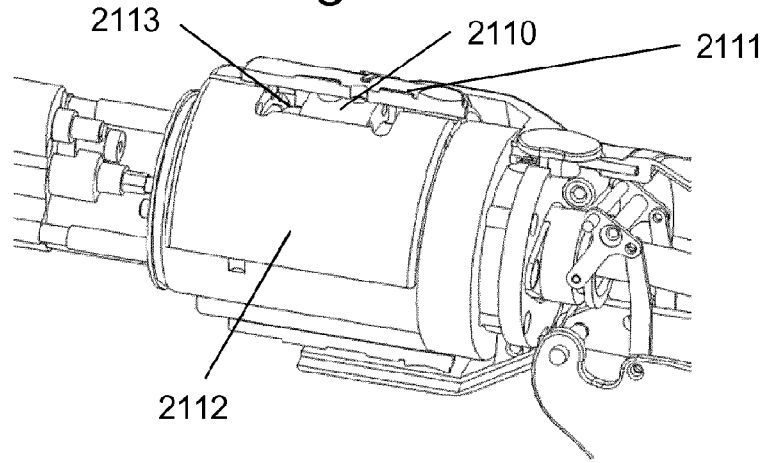
FIG. 14 is another enlarged perspective view of the controlling means of the actuation unit of the surgical instrument of the invention.

As illustrated in FIG. 13, the finger control system is composed by an outer knob 2111 with a magnet 2110, which is mounted in translation on an inner knob 2112, wherein said inner knob 2112 is mounted in axial rotation within the actuation unit 2. Preferably, the inner knob 2112 is mounted in axial rotation on an external housing 2114 forming the sealed compartment of the actuation unit 2.

The magnet 2110 is embedded in or linked to the outer control knob 2111, said outer knob 2111 being easily movable by the fingers of the user. The magnet 2111 can be over-molded in resin or silicone for protection.

When the outer knob 2111 is translated with respect to inner knob 2112, then the magnet 2110 slides in a groove 2113 provided in the inner knob 2112. When the outer knob 2111 is axially rotated on the actuation unit 2, it drives the inner knob 2112 in the same movement.

In a preferred embodiment, the electronics 210 of the controlling means 21 comprises eight Hall sensors 2100. Four of these Hall sensors are used for the distal mobility of the distal tool 5, i.e. for bend/unbend and right/left rotation actuation. The four additional Hall sensors are positioned in the diagonals to allow for combined movements.

One further advantage of the arrangement described above is that there is a single joystick, i.e. the outer knob 2111 that enables the user of the surgical instrument to control the distal mobility of the distal tool 5. Further, both movements (translation, axial rotation) can be actuated independently or simultaneously via the outer knob 2111.

Moreover, the use of Hall sensors 2100 has the advantage that they have the ability to be used as potentiometer and not only as on/off switches. Indeed, the control signal is dependent on the distance of the magnet relative to the corresponding Hall sensor. Therefore when it is desired to have a distal mobility proportional with the displacement of the magnet, then the electronics are configured so that the Hall sensors are used as potentiometers. For instance, it enables the user to control not only the type of movement he wants to provide to the distal tool but also the speed of this movement, the torque, etc.

It should be noted that the above described controlling means of motorized means could be used in many types of surgical instruments, such that the corresponding teaching is not limited for use in the surgical instrument presented here.

In particular, it could be used in a surgical instrument with a handle provided or not with a lever mechanically coupled to the distal tool for actuation of said distal tool via an actuation cable extending coaxially within said elongated arm and rotation shaft. In case there is no such lever on the handle, the actuation unit may further comprises complementary motorized means for actuation of said distal tool via an actuation cable extending coaxially within said elongated arm and rotation shaft. The corresponding controlling means could thus be associated or combined with the above described controlling means of the first motorized means.

Another aspect of the surgical instrument concerns the mechanism in the actuation unit for actuating the bending/unbending of the distal tool 5, i.e. the rotation movement of the distal tool around the pivot axis orthogonal to the longitudinal axis.

As mentioned above, the distal tool 5 is oriented distally by bending/unbending the elongated arm 3 at the pivot joint of the distal member 30. Such bending/unbending is made possible by the presence of two actuation cables (312, 314) running along the elongated arm 3. More precisely, bending is achieved by pulling on one 314 of the actuation cables and simultaneously releasing the other one 312 of the actuation cables, whereas unbending is achieved by pulling on the second cable 312 and releasing the first 314.

Figure 15:
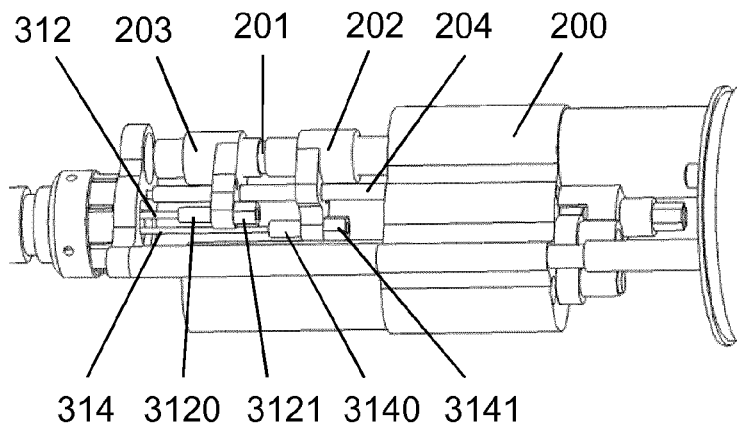
FIG. 15 is an enlarged perspective view of the motorized means of the actuation unit of the surgical instrument of the invention.
Figure 16:
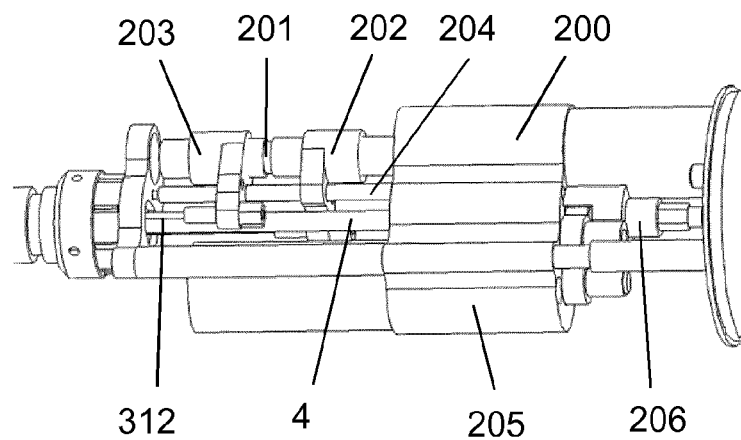
FIG. 16 is another enlarged perspective view of the motorized means of the actuation unit of the surgical instrument of the invention.

As illustrated on FIGS. 15 and 16, the specific motorized actuation mechanism which is proposed is such that the motorized means comprise a motor 200 with a driving shaft 201 having first 202 and second 203 transmission members for coupling the driving shaft 201 with the first 314 and second 312 actuation cables respectively, wherein the first transmission member 202 comprises means for translating the first actuation cable 314 in a first direction collinear to the longitudinal axis upon clockwise rotation of the driving shaft 201, and the second transmission member 203 comprises means for translating the second actuation cable 312 in the first direction upon anticlockwise rotation of the driving shaft 201.

It is preferred that the first 202 and second 203 transmission members are coupled to the driving shaft 201 with coupling means adapted for translating the transmission members (202, 203) in opposite directions along the longitudinal axis when the driving shaft 201 of the motor 200 rotates.

For instance, the coupling means are adapted for translating the first transmission member 202 in the first direction and for translating the second transmission member 203 in a second direction opposite the first direction upon clockwise rotation of the driving shaft 201, and for translating the second transmission member 203 in the first direction and for translating the first transmission member 202 in the second direction upon anticlockwise rotation of the driving shaft 201.

Preferably, the driving shaft 201 comprises two threaded portions of opposite threads (for instance a clockwise thread at motor exit and a counter clockwise thread further away on the axis). One transmission member (202, 203) is mounted on each thread so that such transmission members (202, 203) translate in opposite directions when the driving shaft 201 of the motor 200 rotates. Each of the two bending/unbending cables (314, 312) is coupled to one of the transmission member (202, 203).

As the two threads are opposite, when the motor 200 turns in one direction, one of the transmission members (202, 203) translates one way thus for instance pulls one actuation cable (312, 314) and the other translates the other way then releasing the other cable (312, 314). Motor shaft axial rotation movement then creates bending or unbending of the elongated arm 3.

The two threads could either have the same pitch so that one motor full rotation will move both transmission members (202, 203) the same distance in translation (in opposite direction), or the two threads could have different pitches, to create asymmetric translation of the transmission members (202, 203), as one of the cable will be pulled more in distance than the other is released. This latter arrangement can be useful as one of the actuation cables (312, 314) runs along the long curve of the elongated arm 3 whereas the other runs along the short curve of the elongated arm 3.

The transmission members (202, 203) may further be translatable along a guiding shaft 204 provided for preventing the transmission members (202, 203) to rotate. Further, there can be provided a movable spring on such a guiding shaft 204, positioned between the transmission members (202, 203). Thus, when the transmission members (202, 203) are close to one another, the movable spring is stressed, such that such spring helps the transmission members (202, 203) to translate in opposite directions.

There could also be provided a colar, formed in a soft or hard material, mounted on the driving shaft 201 between the transmission members (202, 203), preferably movable, and forming a stop abutment when the transmission members (202, 203) are translated toward one another. Such a colar could also be provided on one end or the other, or on both ends, of the driving shaft 201 to form a stop abutment when the transmission members (202, 203) are translated in the other direction. Alternatively or additionally, such colar(s) could be similarly provided on the guiding shaft 204.

According to a preferred embodiment, each actuation cable comprises an abutment adapted to cooperate with the corresponding transmission member so that translation of such transmission member in one direction causes the actuation cable to translate in said first direction, whereas a translation of said transmission member in another direction opposite the first direction releases the actuation cable.

Preferably, each actuation cable comprises an end (3140, 3120) with a cylindrical element having a threaded portion. The abutment is formed by a threaded bolt (3141, 3121) mounted on said threaded portion. Further said bolt (3141, 3121) enables adjustment of the length of the actuation cables.

According to another embodiment, the first transmission member comprises means for translating the first actuation cable in a second direction opposite to the first direction upon anticlockwise rotation of the driving shaft, and the second transmission member comprises means for translating the second actuation cable in the second direction upon clockwise rotation of the driving shaft.

Preferably, each actuation cable has an end securely fastened to the corresponding transmission member.

Preferably, the motorized means 20 comprise another motor 205 with another driving shaft 206 fixed to an end of the rotation shaft 4 for actuating rotation of the distal tool 5 around the axis collinear to the own axis of said distal tool 5.

Even though the above actuation mechanism of the bending/unbending is presented with reference to the surgical instrument with a rotatable pistol-grip handle, it should be noted that it could be used in any other types of surgical instrument that uses two actuation cables for controlling the rotation of an arm, such as the surgical instruments as described in WO2010112608 and WO2010112609, that do not necessarily have a rotatable handle.

The proposed actuation mechanism is very advantageous as it is very simple to manufacture. It namely comprises a single motor for actuating both actuation cables (312, 314), which is of great asset, in particular with regard to compactness of the actuation unit and thus of the surgical instrument. Not only is it cheaper and simpler to manufacture, it also enables a more accurate control of the bending/unbending of the distal tool.

BIBLIOGRAPHIC REFERENCES

U.S. Pat. No. 7,147,650
U.S. Pat. No. 7,338,513
U.S. Pat. No. 7,686,826
U.S. Pat. No. 7,842,028
US2006111210
US2007250113
US2010286480
US2010331860
WO2010112608
WO2010112609
WO2011013100
US2010249497

The invention claimed is:
1. A surgical instrument comprising:
an elongated arm extending along a longitudinal axis and having a distal member mounted at a distal end of the elongated arm with means forming a pivot joint around a pivot axis orthogonal to the longitudinal axis;
a rotation shaft coaxial with the elongated arm comprising means forming a universal joint facing the pivot joint;
a distal tool securely fastened at a distal end of the rotation shaft and rotatably mounted on and in the extension of the distal member of the elongated arm, such that the distal tool has two rotational degrees of freedom, distinct and independent of each other, one degree of freedom being around the pivot axis and the other degree of freedom being around an axis collinear to an own axis of the distal tool;
an actuation unit mounted on and in the extension of a proximal end of the elongated arm, said actuation unit comprising motorized means for actuating the motion of the distal tool through at least one of the two rotational degrees of freedom and further comprising controlling means for a user to control the motorized means;
a handle extending from the actuation unit and comprising a lever mechanically coupled to the distal tool for actuation of said distal tool via an actuation cable extending coaxially within said elongated arm and rotation shaft;

wherein the handle has a non-axially-symmetric shape and is mounted on and in the extension of the actuation unit with coupling means enabling rotation of the handle relative to the actuation unit around the longitudinal axis, and the actuation unit comprises a casing that encompasses both the motorized means and the controlling means, said casing comprising prehensile means for holding the surgical instrument while rotating the handle and the actuation unit relative to one another, and wherein the controlling means comprises electronic components for actuation of the motorized means and switch elements for the user to control the electronic components, wherein the switch elements comprise an outer switch element arranged on the casing in a way to be operated by the user whatever the rotational position of the handle relative to the actuation unit.

2. The surgical instrument of claim 1, wherein the lever is coupled to the actuation cable through a non-axial transmission mechanism for enabling an electric cable to run axially out of the actuation unit along the longitudinal axis from the motorized means to the handle.

3. The surgical instrument of claim 2, wherein the transmission mechanism comprises:
  at least one rod arranged within the actuation unit offset of the longitudinal axis, said rod being translatable along an axis parallel to the longitudinal axis;
  a coupling member between said rod and the actuation cable, said coupling member being shaped and arranged to transmit the translation motion of the rod to the actuation cable and to enable a free rotation of the actuation cable around the longitudinal axis;
  an annular member arranged within the actuation unit to be coupled with the lever of the handle, said annular member being fixed to an end of said rod, and said annular member being arranged to surround the electric cable and to be translatable along an axis parallel to the longitudinal axis;
  and wherein the annular member further comprises a circular groove for insertion of at least two pins provided at an end of the lever, said circular groove and pins forming a coupling enabling the lever to cause the annular member and rod to translate while enabling a free rotation of the handle and lever relative to the actuation unit.

4. The surgical instrument of claim 1, wherein the motorized means and electronic components are enclosed in a sealed compartment.

5. The surgical instrument of claim 4, wherein the switch elements are located out of the sealed compartment.

6. The surgical instrument of claim 5, wherein the switch elements comprise at least one magnet for contactless signal transmission to hall sensors of the electronic components.

7. The surgical instrument of claim 6, wherein the at least one magnet is mounted on the sealed compartment and arranged to be displaced through two different degrees of freedom in order to vary the position of the magnet relative to the hall sensors.

8. The surgical instrument of claim 6, wherein the switch elements comprise one magnet, an outer knob and an inner knob, wherein the magnet is fastened to the outer knob and is mounted in translation within a longitudinal groove provided in the inner knob along an axis parallel to the longitudinal axis, said inner knob being rotatably mounted around the longitudinal axis.

9. The surgical instrument of claim 6, wherein the switch elements comprise at least eight hall sensors, two of said at least eight hall sensors being arranged for providing signal to the motorized means upon translation of the outer knob, two others of said at least eight hall sensors being arranged for providing signal to the motorized means upon rotation of an outer knob, and the four remaining of said at least eight hall sensors being arranged for providing signal to the motorized means upon combined translation and rotation of the outer knob.

10. The surgical instrument of claim 6, wherein the hall sensors are used as potentiometers.

11. The surgical instrument of claim 10, wherein the hall sensors are used for controlling the speed of the motorized means.

12. The surgical instrument of claim 6, wherein a translation of the outer knob controls the motorized means for actuation of the distal tool through a rotation around the pivot axis, and wherein a rotation of an outer knob controls the motorized means for actuation of the distal tool through a rotation around the axis collinear to the own axis of the distal tool.

13. The surgical instrument of claim 1, wherein the coupling means comprise a clutch assembly for preventing rotation of the handle relative to the actuation unit.

14. The surgical instrument of claim 1, wherein the casing of the actuation unit has a cylindrical shape and the outer switch element is an annular joystick arranged around the casing of the actuation unit to provide to the user a finger control of the motorized means.

15. A surgical instrument comprising:
  an elongated arm extending along a longitudinal axis and having a distal member mounted at a distal end of the elongated arm with a pivot joint structure around a pivot axis orthogonal to the longitudinal axis;
  a rotation shaft coaxial with the elongated arm comprising a universal joint structure facing the pivot joint structure;
  a distal tool securely fastened at a distal end of the rotation shaft and rotatably mounted on and in the extension of the distal member of the elongated arm, such that the distal tool has two rotational degrees of freedom, distinct and independent of each other, one degree of freedom being around the pivot axis and the other degree of freedom being around an axis collinear to an own axis of the distal tool;
  an actuation unit mounted on and in the extension of a proximal end of the elongated arm, said actuation unit comprising motors configured to actuate the motion of the distal tool through at least one of the two rotational degrees of freedom and further comprising controlling elements configured to enable a user to control the motors;
  a handle extending from the actuation unit and comprising a lever mechanically coupled to the distal tool for actuation of said distal tool via an actuation cable extending coaxially within said elongated arm and rotation shaft;
  wherein the handle has a non-axially-symmetric shape and is mounted on and in the extension of the actuation unit with a coupling structure enabling rotation of the handle relative to the actuation unit around the longitudinal axis, and the actuation unit comprises a casing that encompasses both the motors and the controlling elements, said casing comprising a prehensile structure for holding the surgical instrument while rotating the handle and the actuation unit relative to one another, and wherein the controlling elements comprise electronic components for actuation of the motorized means and switch elements for the user to control the electronic components, wherein the switch elements comprise an outer switch element arranged on the casing in a way to be operated by the user whatever the rotational position of the handle relative to the actuation unit.

16. A surgical instrument comprising:
- an elongated arm extending along a longitudinal axis and having a distal member mounted at a distal end of the elongated arm with a pivot joint structure around a pivot axis orthogonal to the longitudinal axis;
- a rotation shaft coaxial with the elongated arm comprising a universal joint structure facing the pivot joint structure;
- a distal tool securely fastened at a distal end of the rotation shaft and rotatably mounted on and in the extension of the distal member of the elongated arm, such that the distal tool has two rotational degrees of freedom, distinct and independent of each other, one degree of freedom being around the pivot axis and the other degree of freedom being around an axis collinear to an own axis of the distal tool;
- an actuation unit mounted on and in the extension of a proximal end of the elongated arm, said actuation unit comprising motors configured to actuate the motion of the distal tool through at least one of the two rotational degrees of freedom and further comprising a switch configured to enable a user to control the motors;
- a handle extending from the actuation unit and comprising a lever mechanically coupled to the distal tool for actuation of said distal tool via an actuation cable extending coaxially within said elongated arm and rotation shaft;
- wherein the handle has a non-axially-symmetric shape and is mounted on and in the extension of the actuation unit with a coupling structure enabling rotation of the handle relative to the actuation unit around the longitudinal axis, and the actuation unit comprises a casing that encompasses both the motors and the switch, said casing comprising a prehensile structure for holding the surgical instrument while rotating the handle and the actuation unit relative to one another;
- wherein the switch is adapted to be operated by the user whatever the rotational position of the handle relative to the actuation unit; and
- wherein the lever is coupled to the actuation cable through a non-axial transmission mechanism for enabling an electric cable to run axially out of the actuation unit along the longitudinal axis from the motors to the handle.

* * * * *